United States Patent [19]

Reineman

[11] Patent Number: 5,522,856

[45] Date of Patent: Jun. 4, 1996

[54] PACEMAKER WITH IMPROVED SHELF STORAGE CAPACITY

[75] Inventor: Henk Reineman, Zuthpen, Netherlands

[73] Assignee: Vitatron Medical, B.V., Dieren, Netherlands

[21] Appl. No.: 309,070

[22] Filed: Sep. 20, 1994

[51] Int. Cl.[6] .................. A61N 1/372; A61N 1/362
[52] U.S. Cl. .................... 607/9; 607/16; 607/34
[58] Field of Search .................. 607/9, 27, 34, 607/16

[56] References Cited

U.S. PATENT DOCUMENTS

| | | | |
|---|---|---|---|
| 3,926,197 | 12/1975 | Alley, III | 607/9 |
| 4,404,972 | 9/1983 | Gordon et al. | 607/16 |
| 4,556,061 | 12/1985 | Barreras et al. | 128/419 PT |
| 5,022,395 | 6/1991 | Russie | 607/16 |
| 5,237,991 | 8/1993 | Baker, Jr. et al. | 607/27 |
| 5,350,407 | 9/1994 | McClure et al. | 607/16 |
| 5,370,666 | 12/1994 | Lindberg et al. | 607/34 |

*Primary Examiner*—William E. Kamm
*Assistant Examiner*—Carl H. Layno
*Attorney, Agent, or Firm*—Woodcock Washburn Kurtz Mackiewicz & Norris

[57] ABSTRACT

A pacemaker has logic incorporated for holding the pacemaker circuitry, or at least a portion of such circuitry, in a low current drain "standby" mode of operation from time of fabrication until time of implantation or preparation for implantation, in order to minimize battery depletion during shelf life. In one embodiment, the pacemaker detects when a lead has been connected to the pulse generator output so as to present an impedance below a predetermined threshold, and such detection is used to take the pacemaker out of the "standby" mode and place it in a fully operational mode. The pacemaker is further provided for sensing an externally generated signal in response to which the pacemaker is placed in an operational mode for a predetermined time duration, following which it reverts to the standby mode.

7 Claims, 2 Drawing Sheets

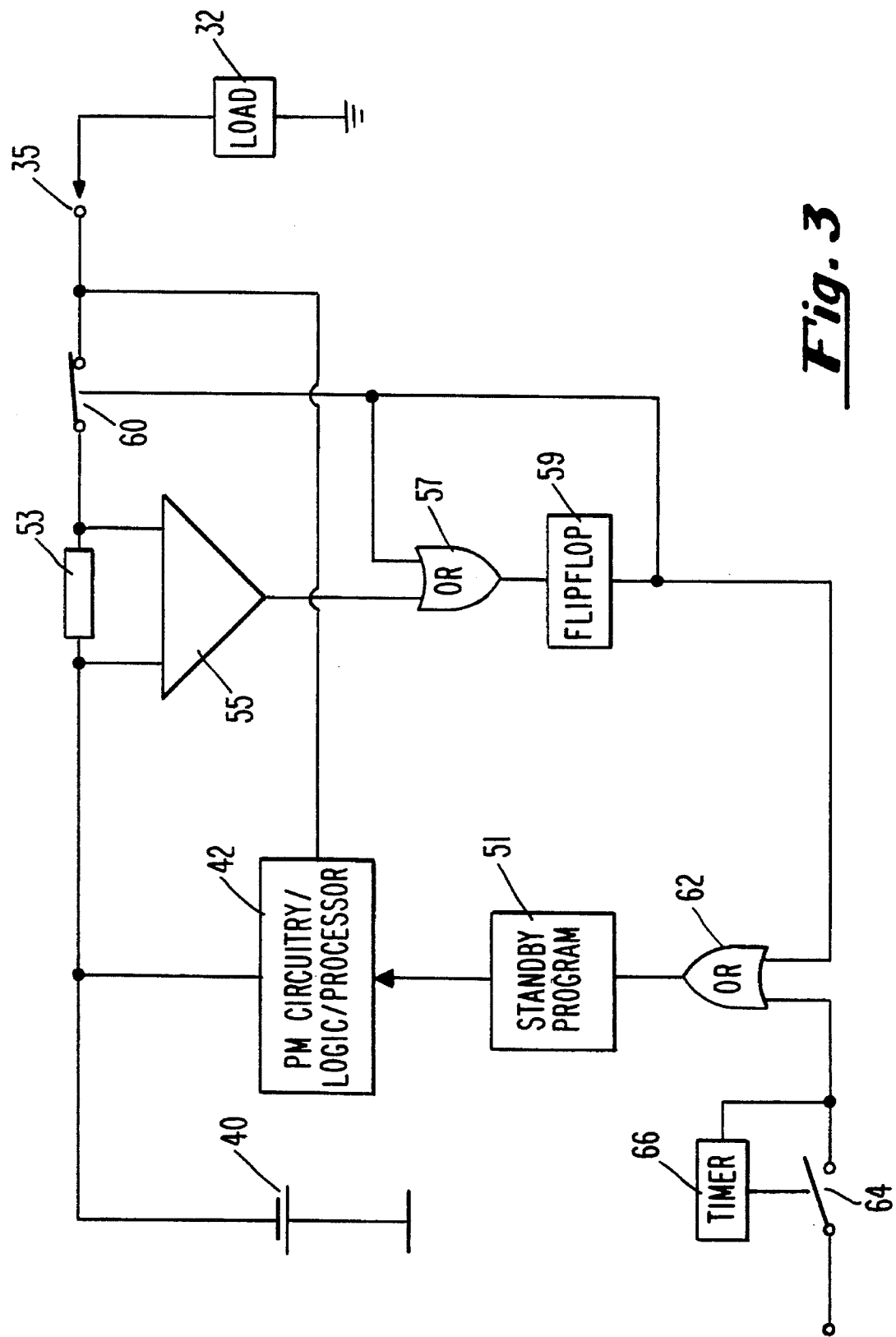

PACEMAKER WITH IMPROVED SHELF STORAGE CAPACITY

FIELD OF THE INVENTION

This invention relates to cardiac pacemaker systems and, more particularly, pacemakers having hardware and/or software for switching between a low power standby mode of operation and full power operation.

BACKGROUND OF THE INVENTION

The capacity of implantable cardiac pacemakers to perform multiple functions over the lifespan of a significant number of years has improved dramatically with technological advances. Thus, today's pacemakers often feature the ability to operate in different modes, to adapt pacing rate to sensed physiological parameters, to store significant information regarding pacemaker operation and sensed patient events, to detect and respond to tachycardia and to perform a number of other important and significant functions over and above delivering pace pulses. A modern pacemaker can be programmed by an external programmer, and can both receive information from an external source and transmit collected data to an external source. Most present day pacemakers employ a microprocessor or some sort of microprocessor logic for software control of a number of the pacemaker operating functions. However, despite vast improvements in pacemaker batteries and in miniaturization and efficiency of microprocessors and other components, providing for all of these functions and operations makes a substantial demand on the pacemaker's battery. The lifetime for presently available implantable pacemakers varies within a range of about 5–10 years. For certain smaller pacemakers, the usable lifetime may be in the order of 5–6 years.

Whether or not the pacemaker industry can look forward to improvements in battery design and capacity, there is an ongoing need to improve pacemaker technology to the extent possible to decrease battery drain, and thus maximize the usable lifetime of the pacemaker, whether it is a relatively small or a relatively large design pacemaker. For this reason, there have been a number of improvements designed to minimize current drain of the pacemaker when in operation. Many pacemaker designs incorporate what is referred to as a "sleep mode" feature, whereby the microprocessor is operated at a lower clock frequency during a portion of each pacemaker cycle when it is not actually carrying out instructions. This technique reduces the current drain of the microprocessor for the periods when it is in the sleep mode, or standby mode. Another relatively old technique is to use an external magnetic signal and a reed switch in the implanted pacemaker, arranged to disconnect a circuit from the pacemaker battery when the circuit is not going to be utilized.

The specific problem that this invention addresses, and which presently represents a significant need in the art, is that of increasing the shelf life of the pacemaker, i.e., minimizing the current drain of the pacemaker after its fabrication has been completed and until the time that it is actually implanted in a patient. For a typical current model small pacemaker having a lifetime of 5–6 years, the shelf current drain can be as great as 10 microamps. If the pacemaker spends a year from time of fabrication until it is implanted, i.e., on the shelf, it can discharge approximately 10% of its capacity during that year, thus significantly reducing its usable lifetime. However, if the shelf current drain can be reduced from about 10 microamps to about 2.5–3.5 microamps, it is apparent that the usable operational lifetime of the pacemaker can be increased.

There have been some attempts to avoid current drain prior to actual implantation, and thus minimize battery depletion during shelf life. Thus, Vitatron Medical, B.V., assignee of this invention, had an early 1960's model where the pacemaker was turned on by screwing on the indifferent plate at the time that implantation was anticipated. Other pacemaker models manufactured by Medtronic, Inc., entailed similar type of pacemaker turn-on by use of a "pigtail" connected battery. However, these techniques are not currently useful in view of modern techniques for manufacturing and sealing the pacemaker so as to maintain long life integrity of the pacemaker against ingress of body fluids. Another technique that has been utilized by Medtronic, Inc., in connection with its Activitrax™ pacemaker, has been to ship the pacemaker at a relatively low non-rate responsive mode, so that until it is implanted it operates at a reduced rate and relatively low current drain. At the time of implantation, the pacemaker is programmed to the rate responsive mode, where it operates at a relatively higher current drain. While this technique affords a distinct savings in current drain for the duration of the shelf life, it is limited to taking advantage of only the current drain savings that results from operating at a lower base pacing rate. By contrast, this invention seeks to take advantage of all opportunities to reduce current drain during shelf life, and still provide a safe and reliable means for switching from a low power standby mode to a full power operational mode when implantation is imminent.

SUMMARY OF THE INVENTION

It is an object of this invention to provide a pacemaker system having an implantable pacemaker to be used in conjunction with a pacing lead interconnecting the pacemaker and the patient's heart, the pacemaker having hardware and software for holding as much as the pacemaker circuitry as possible in a low power standby mode until the pacemaker is being prepared for implantation. The pacemaker has sensing means for determining when the pacemaker is being connected for implantation, and responds to such sensing by removing the pacemaker circuitry from standby mode. Additionally, the pacemaker incorporates means for enabling the pacemaker to go into its operational mode for a predetermined time duration prior to implantation, while returning the pacemaker to the minimized standby current mode during its remaining storage time.

BRIEF DESCRIPTION OF THE DRAWINGS

FIG. 3 is a more specific circuit diagram of a preferred embodiment of the invention.

DESCRIPTION OF THE PREFERRED EMBODIMENTS

Figure 1:
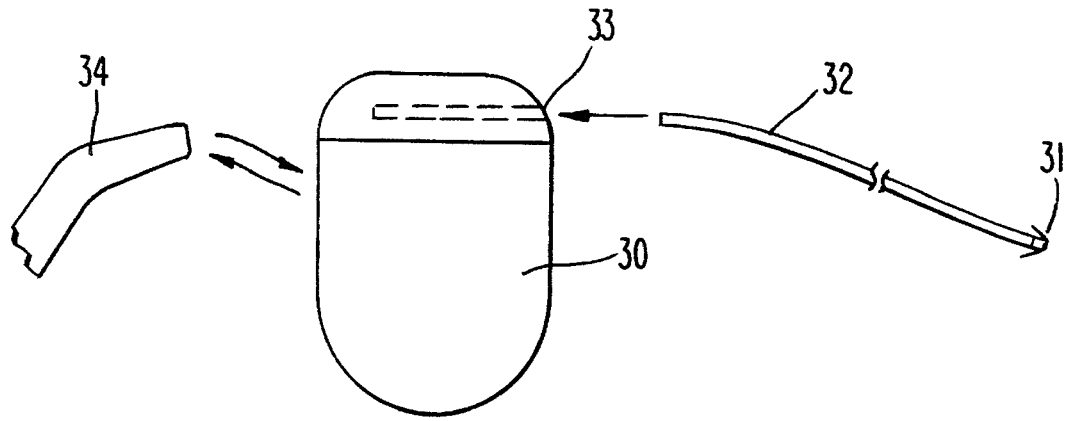
FIG. 1 is a representation of the three major components of the pacing system of this invention, i.e., a pacemaker, a lead, and a programmer.

Referring now to FIG. 1, there is presented an illustration of the apparatus of the system of this invention. A pacemaker 30 of any suitable design for implantation into a human body, contains the standard components and circuits that are used in a modern pacemaker. Thus, it contains one or more batteries to provide power. It contains electronic circuitry, in any modern form and preferably including one or more microprocessor chips, for carrying out all the required logic to enable the pacemaker to deliver pace pulses when appropriate and at a programmed rate and energy level. The pacemaker also suitably includes memory for holding logic instructions and storing information that has been obtained from the patient's heart, for monitoring pacemaker characteristics, or for holding data received from an external source via known programming means 34. The pacemaker also contains a receiving means 33 for receiving a lead 32 which provides the electrical connection between the pacemaker and the patient's heart. Lead 32 may be any standard pacemaker lead and has a proximal portion which is adapted to interconnect securely to the pacemaker, both mechanically and electrically. It may have either a unipolar or bipolar electrode arrangement, comprising at least one electrode 31 at the distal end for electrical interface with the patient's heart. As is well known, cardiac pace pulses generated by the pacemaker are delivered through the lead to the patient's heart, and likewise the electrode system on the lead senses naturally occurring cardiac signals and transmits them back to the pacemaker for analysis and use in controlling pacemaker operation. It is to be understood that this invention is not limited to the hardware or software configuration of the pacemaker or the details of the lead with which it is used. Load 32 may be in fact a unipolar or bipolar lead, positioned to deliver pace pulses either to a patient's ventricle, atrium, or both atrium and ventricle, and likewise to transmit sense signals from the patient's heart back to the pacemaker. Likewise, any sort of programming arrangement might be used for communication between the pacemaker 30 and an external programmer unit illustrated at 34.

Figure 2:
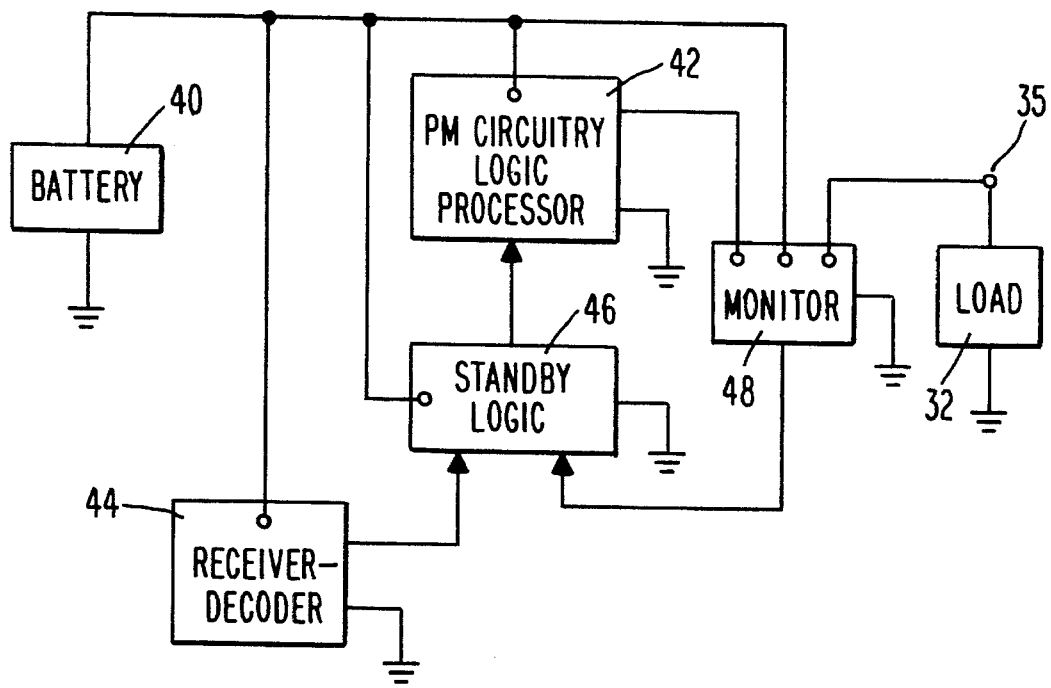
FIG. 2 is a representative block diagram of the major component blocks of a pacemaker of this invention.

Referring now to FIG. 2, there are shown the primary features of the pacemaker of this invention. A battery 40 is suitably a modern lithium-type battery. Although characteristics of pacemaker batteries may vary, a nominal output prior to "end of life" is 2.8 volts. Any type of battery which is suitable for an implanted pacemaker, or combination of batteries, may be employed. A receiver-decoder circuit 44 is illustrated, which is powered by the source 40. The receiver-decoder constitutes conventional circuitry and comprises a receiver for receiving programmer signals from programmer 34, and decoding them. While a conventional modern day pacemaker may be programmed a great number of different ways, for purposes of illustrating this invention the discussion is directed to receiving signals used for controlling when the pacemaker circuitry is in either a normal operational mode or in a standby mode. As used in this disclosure, operational mode means that the pacemaker is enabled to be normally and fully operational subject to programming restrictions, such that it is drawing a normal operational current load from the battery. In the standby mode, some, most, or essentially all of the pacemaker circuitry, including any microprocessor utilized in the pacemaker, is in a mode of operation where it is drawing a reduced current level from the battery source 40. Decoded signals from block 44 are inputted into standby logic circuit 46, likewise powered by the battery. Standby logic circuit 46 is designed to provide a combination of outputs which control when the pacemaker circuitry in block 42 is in a standby or operational mode. Thus, the output of block 46 may be a single logic line or a number of logic lines which are connected to respective circuit points in block 42 so as to place the pacemaker into either operational or standby mode of operation. As illustrated, the pacemaker circuitry block 42 includes logic and processor circuitry, and is likewise powered by battery 40. An output from block 42 is shown connected through block 48 to pacemaker output terminal 35 to which lead 32 is connected when the system is implanted. Of course, during normal operation of the implanted system, monitor 48 must present an essential direct connection from the pulse generator output to the terminal 35.

Still referring to FIG. 2, it is seen that block 48, designated monitor, is connected to the battery 40 and also to the pacemaker block 42. Block 48 carries out the function of monitoring the status of the pacemaker to determine when it is connected to a load, i.e., to a lead positioned in the heart, so as to be capable of delivering cardiac signals. As discussed below in a preferred embodiment, one technique is to monitor the current flowing from the battery 40 through a fixed value resistance in monitor circuit 48 to the load, to determine when a load indeed has been connected to the output terminal(s) of the pacemaker. When such circumstance has been detected, the monitor circuit 48 provides an output to standby logic circuit 46, which provides an output so as to take the pacemaker out of standby operation and place it into the operational mode. In another embodiment, the monitor determines when there is an actual delivery of current pulses corresponding to pacemaker pulses which are delivered to the output, indicating that pace pulses are being delivered to a patient's heart through the lead 32. Again, in that situation, an output signal is delivered from the monitor block 48 to standby logic 46.

In another feature of this invention, the pacemaker may be removed from storage and tested for functionality, i.e., to determine that it is fully operational, and then returned to storage in the standby mode. In this arrangement, the physician uses the programmer 34 to deliver a predetermined coded signal to block 44. When the signal for temporary operational mode is received, a suitable logic output is connected to standby logic block 46, which times out a signal of predetermined duration which is used to control block 42 in the operational mode for the length of the duration. Thus, a signal received at block 44 can cause an output from block 46 for a length of 30 minutes, which causes the pacemaker circuitry to go into operational mode for 30 minutes, following which circuitry 42 reverts to standby mode. Alternately, a first signal can be received at circuit 44 for causing the pacemaker circuitry to be taken out of standby mode, and a subsequently received second signal can return the pacemaker to standby mode. By way of example, when the pacemaker is first manufactured, it may be set to operate at a low pacing rate, i.e., a rate considerably lower than the normal lower rate limit, e.g., 30 ppm. Thus, during normal shelf life, with the pacemaker circuitry operating at the low rate (and with no output pulses actually being delivered), current drain is very low. A signal received at decoder 44 can be decoded to cause standby logic circuit 46 to cause pacemaker circuitry 42 to generate pace pulses at the normal rate (whether or not subject to rate control). When it is desired to return to standby, a signal received from programmer 34 is decoded and used by logic circuit 46 to return the pacing rate to 30 ppm.

Reviewing the options provided the pacemaker system of this invention, in each embodiment the pacemaker is initially placed in a standby mode of operation upon completion of manufacture. In all modes, it stays in standby until there is detection of some criterion for going to the operational mode. In this way, current drain from the battery source is minimized until the pacemaker is actually implanted.

In a first embodiment, the pacemaker senses when a lead is coupled to the pacemaker implanted such that the impedance load seen at the output terminals is below a predetermined level. Once this has occurred, the pacemaker remains permanently in the operational mode.

In a second embodiment, the first embodiment is supplemented by also providing programmer means for temporarily switching the pacemaker from standby to operational mode before time of implant. For example, the use of a reed switch in the pacemaker in combination with a programming signal enables a user to switch the pacemaker into operational mode for a selected period of time, e.g., 30 minutes, during which the pacemaker can be tested or otherwise checked. Following timeout of the 30 minute duration the pacemaker automatically returns to the standby mode.

In another embodiment, the pacemaker monitors when generation of output signals is accompanied by actual delivery of current pulses to the load, thereby detecting implantation and switching the pacemaker permanently from standby to operational mode. This embodiment also can be combined with the feature of enabling a temporary switch from standby to operational mode.

In yet another embodiment the pacemaker can be set at the factory to an operational rate below the normal pacing range, and detection of this low rate holds selected pacemaker circuitry in standby operation. When the user programs the pacemaker to any rate within an allowed pacer range between LRL and URL, the pacemaker automatically switches from standby to operational mode. The pacemaker can be returned to a standby mode by another program signal which specifically sets the pacing rate back to the initial factory-set low rate. Thus, in this embodiment, the user can switch from standby to operational or vice versa at any time by programming either a predetermined low rate or any normal rate into the pacemaker.

Referring now to FIG. 3, there is shown a specific embodiment of the invention. This embodiment illustrates a system where a lead 32 having a resistance less than a predetermined amount is connected to the pacemaker at implant or during a preimplant procedure. The connection of this load into a simple series line with battery 40 and a resistor 53 of predetermined resistance enables detection of the load connection to the pacemaker, and results in switching from standby to operational mode. This system also enables a single transmission by the user from an external source to the pacemaker, which suitably has a reed switch, the closure of which reed switch switches the pacemaker from standby to operational mode for a predetermined period of time, e.g., 30 minutes, after which the device returns to the standby mode. In FIG. 3, standby program 51 is initially set at the factory to produce outputs coupled to circuitry 42 that hold it in a standby mode of operation. Standby program 51 holds the circuitry 42 in standby unless it receives a logic high (1) signal from gate 62.

As seen in FIG. 3, there is a battery illustrated at 40, shown as having its positive terminal connected to ground, suitably the pacemaker case. There is a single resistor, indicated at 53, connected through a switch 60 to the output terminal 35. When a load 32, in the form of a lead, is connected between output terminal 35 and system ground, there is a current flow from the battery source, the amount of which is determined by the combined sizes of resistor 53 and load 32. Although lead loads may vary, for purposes of illustration a lead load in this example is defined as less than 25 k. By making resistor 53 50 k, for a battery voltage of 2.8 volts a current of 37.33 microamps flows when the lead 32 is connected to the system. Comparator 55 senses the voltage across resistor 53, and is set to determine when a current greater than 35 microamps flows. When this is detected, a signal is produced at the output of comparator 55 and gated through OR gate 57 to flip flop 59. Flip flop 59 is reset during the manufacturing process, in which state it connects a logic low signal to OR gate 62. When flip flop 59 is set by the signal received from OR gate 57, this produces a logic high signal at the flip flop output, which is looped around through gate 57 to clamp or latch the flip flop in a set condition. The output of flip flop 59 is also connected so as to open switch 60, such that thereafter resistor 53 is taken out of the circuitry. The logic 1 signal from flip flop 59 is also gated to OR gate 62, where it is gated through and disables standby program 51, such that circuitry block 42 is caused to revert to a normal operational mode.

The arrangement of FIG. 3 also provides for a reed switch 64 which, as shown, is normally open. Upon receipt of a signal from an external source, the reed switch closes, causing a logic high signal to be gated through OR gate 62 to disable the standby program 51. When this happens, the circuitry 42 goes into operational mode. The switching of reed switch 64 initiates a time out at timer 66 of 30 minutes, or any predetermined time period, during which time the switch is latched closed. At the end of the duration the switch is opened, an enable signal is gated through OR gate 62 and the standby program 51 produces the necessary output to return circuitry 42 to the standby mode.

As stated above, it is within the scope of this invention to place the pacemaker circuitry into any version of standby mode prior to actual system operation, wherein there is a reduction of current drain as compared to being in the normal operational mode. For example, the standby logic can receive a simple high-low logic signal from the monitor, a logic 1 for standby, and a logic 0 for normal operation. The clock signal is passed through a 100:1 rate divider and connected to a first input of a first AND gate, and the standby signal is connected to the second signal of the first AND gate. The clock signal is connected directly to a first input of a second AND gate, and the standby signal is inverted and then connected to a second input of the second AND gate. The outputs of the two AND gates are connected through an OR gate to the microprocessor, so that the clock rate is reduced by 100 when in standby mode, and normal when in operational mode.

Additionally, the pacer can be equipped with a low power simple back-up pacer, with all other circuitry switched off during standby, and switched on when a lead is connected; the switches are operated by the standby signal. Also, a DDD pacer can be programmed to operate only in a mode where just one channel is active during standby, and switched to normal mode operation only when the system is detected as being operational.

It is to be understood that the invention may be practiced by switching any portion of the pacemaker circuitry between standby and operational. Of course, the more circuitry is held in standby while on the shelf, the less battery depletion during shelf time. The invention achieves improved shelf time by incorporating into the pacemaker a fail-safe arrangement for determining when the pacemaker is being prepared to be system operational, i.e., ready for implantation and use in pacing a patient.

What is claimed is:

1. A pacemaker system having an implantable pacemaker with a battery for providing energy, and pacemaker circuitry powered by said battery for carrying out pacemaker functions, said functions including generating pace pulses for delivery to a patient's heart, at least some portion of said pacemaker circuitry having a low current standby mode of operation and a normal operational mode of operation, said system further comprising, when said pacemaker is implanted in a patient, a lead for providing an electrical connection between said pacemaker and said patient, further comprising:

means for initially holding said portion of pacemaker circuitry in said standby mode when said lead is not operatively connected thereto;

detecting means for detecting when said pacemaker and said lead are operatively connected, and response means responsive to said detected connection to place said portion of pacemaker circuitry in said normal operational mode; and wherein said pacemaker circuitry comprises a pace generator which cyclically produces pace pulses in both said standby and operational modes, and wherein said detecting means comprises means for detecting when there is a current above a predetermined threshold associated with pace pulses generated by said pulse generator, thereby sensing when a load has been placed across said pacemaker output.

2. A pacemaker system having an implantable pacemaker with a battery for providing energy, an output, and pacemaker circuitry powered by said battery for carrying out pacemaker functions including generating pace pulses for delivery to said output, at least some portion of said pacemaker circuitry having a low current standby mode of operation and a normal operational mode of operation, said system further comprising, when said pacemaker is implanted in a patient, a lead connected to said output for providing an electrical connection between said pacemaker and said patient, said lead having an impedance in a range less than a predetermined maximum value, said system having standby control means for initially holding said portion of pacemaker circuitry in said standby mode when said lead is not operatively connected to said output, detecting means for detecting a condition which indicates that said pacemaker and said lead are operatively connected, and response means responsive to said detected connection for placing said portion of pacemaker circuitry in said normal operational mode; and said detecting means having a monitoring resistance in series between said battery and said output, said monitoring resistance having an impedance value greater than said predetermined maximum value, and wherein said detecting means detects when a load having an impedance value less than said predetermined maximum value is connected to said output, said pacemaker further comprising temporary means for temporarily responding to an external signal and placing said portion of pacemaker circuitry in said normal operational mode for a temporary time duration.

3. The pacemaker system as described in claim 2, wherein said temporary means further includes a timer and means for triggering said timer with an external signal.

4. The pacemaker as described in claim 2, further comprising latch means for latching said portion of pacemaker circuitry in said normal operational mode after said response means has placed said pacemaker circuitry in said normal operational mode.

5. A pacemaker system having an implantable pacemaker with a battery for providing energy, an output, and pacemaker circuitry powered by said battery for carrying out pacemaker functions including generating pace pulses for delivery to said output, at least some portion of said pacemaker circuitry having a low current standby mode of operation and a normal operational mode of operation, said system further comprising, when said pacemaker is implanted in a patient, a lead connected to said output for providing an electrical connection between said pacemaker and said patient, said lead having an impedance in a range less than a predetermined maximum value, said system having standby control means for initially holding said portion of pacemaker circuitry in said standby mode when said lead is not operatively connected to said output, detecting means for detecting a condition which indicates that said pacemaker and said lead are operatively connected, and response means responsive to said detected connection for placing said portion of pacemaker circuitry in said normal operational mode; and said detecting means having a monitoring resistance in series between said battery and said output, said monitoring resistance having an impedance value greater than said predetermined maximum value, and wherein said detecting means detects when a load having an impedance value less than said predetermined maximum value is connected to said output, said pacemaker further comprising temporary means for temporarily responding to an external signal and placing said portion of pacemaker circuitry in said normal operational mode for a temporary time duration, wherein said pacemaker circuitry comprises a pace generator which cyclically produces pace pulses in both said standby and operational modes, and wherein said detecting means comprises means for detecting when there is a current above a predetermined threshold associated with pace pulses generated by said pulse generator, thereby sensing when a load has been placed across said pacemaker output.

6. The pacemaker system as described in claim 5, wherein said monitoring resistance impedance value is at least twice said predetermined maximum value.

7. The pacemaker system as described in claim 5, wherein said packemaker circuitry produces pace pulses at a predetermined low rate when in said stanby mode, and said standby control means holds said portion of said pacemaker circuitry in a standby mode whenever said pacemaker circuitry produces pace pulses at said low rate and in the operational mode whenever said pacemaker circuitry is controlled to produce pace pulses at said normal rate.

\* \* \* \* \*